(12) United States Patent
Fallin et al.

(10) Patent No.: US 10,149,963 B2
(45) Date of Patent: Dec. 11, 2018

(54) CATHETER ASSEMBLY

(71) Applicant: Vital 5, LLC, Logan, UT (US)

(72) Inventors: Thomas Wade Fallin, Hyde Park, UT (US); Jean-Sebastien Merette, Montreal (CA); Patrick Michel White, West Chester, PA (US)

(73) Assignee: Vital 5, LLC, Logan, UT (US)

( * ) Notice: Subject to any disclaimer, the term of this patent is extended or adjusted under 35 U.S.C. 154(b) by 562 days.

(21) Appl. No.: 14/987,576

(22) Filed: Jan. 4, 2016

(65) Prior Publication Data

US 2016/0206850 A1  Jul. 21, 2016

Related U.S. Application Data

(63) Continuation of application No. 13/240,781, filed on Sep. 22, 2011, now Pat. No. 9,265,913, which is a continuation-in-part of application No. 12/677,870, filed on Jul. 2, 2008, now Pat. No. 8,590,472.

(60) Provisional application No. 61/385,309, filed on Sep. 22, 2010, provisional application No. 61/450,096, filed on Mar. 7, 2011, provisional application No. 61/494,822, filed on Jun. 8, 2011.

(51) Int. Cl.
*A61M 1/00* (2006.01)
*A61M 25/00* (2006.01)

(52) U.S. Cl.
CPC ........ *A61M 25/0071* (2013.01); *A61M 1/008* (2013.01); *A61M 25/0026* (2013.01); *A61M 25/0043* (2013.01); *A61M 25/0068* (2013.01); *A61M 25/0074* (2013.01); *A61M 2025/006* (2013.01); *A61M 2025/0062* (2013.01); *A61M 2025/0073* (2013.01)

(58) Field of Classification Search
CPC .............. A61M 1/008; A61M 25/0026; A61M 25/0043; A61M 25/0068; A61M 25/0071; A61M 25/0074; A61M 2025/006; A61M 2025/0062; A61M 2025/0073
See application file for complete search history.

(56) References Cited

U.S. PATENT DOCUMENTS

| 3,572,340 A | 3/1971 | Lloyd et al. |
| 3,823,720 A | 7/1974 | Tribble |
| 3,854,477 A | 12/1974 | Smith |
| 3,967,728 A | 7/1976 | Gordon et al. |

(Continued)

FOREIGN PATENT DOCUMENTS

| JP | 09-108218 A | 4/1997 |
| JP | 11-319103 | 11/1999 |

(Continued)

OTHER PUBLICATIONS

Prior, David V., "Localised Drug Delivery via Collagen-Based Biodegradable Matrices," The Drug Delivery Companies Report Autumn/Winter 2004, pp. 39-42.

(Continued)

*Primary Examiner* — Lynne Anderson

(57) ABSTRACT

Devices and methods are provided to conduct fluid away from or deliver fluid to an area of a treatment site of a patient's body. In one aspect of the invention, a catheter includes a terminal end with a fluid exchange portion. The terminal end may further include a diffuser. The terminal end may further include a barrier.

20 Claims, 9 Drawing Sheets

(56) References Cited

U.S. PATENT DOCUMENTS

| | | | |
|---|---|---|---|
| 4,048,996 A | 9/1977 | Mittleman et al. |
| 4,364,394 A | 12/1982 | Wilkinson |
| 4,445,897 A | 5/1984 | Ekbladh et al. |
| 4,623,329 A | 11/1986 | Drobish |
| 4,643,716 A | 2/1987 | Drach |
| 4,692,153 A | 9/1987 | Berlin et al. |
| D294,639 S | 3/1988 | Croll |
| 4,786,500 A | 11/1988 | Wong |
| D300,947 S | 5/1989 | Utas-Sjoberg |
| 4,925,452 A | 5/1990 | Melinyshyn et al. |
| 5,034,006 A | 7/1991 | Hosada et al. |
| 5,100,395 A | 3/1992 | Rosenberg |
| 5,120,304 A | 6/1992 | Sasaki |
| 5,201,723 A | 4/1993 | Quinn |
| 5,221,255 A | 6/1993 | Marhukar et al. |
| 5,234,406 A | 8/1993 | Drasner et al. |
| 5,318,517 A | 6/1994 | Reiman |
| 5,320,599 A | 6/1994 | Griep et al. |
| 5,324,518 A | 6/1994 | Orth et al. |
| 5,358,494 A | 10/1994 | Svedman |
| 5,425,723 A | 6/1995 | Wang |
| 5,433,713 A | 7/1995 | Trotta |
| 5,458,582 A | 10/1995 | Nakao et al. |
| 5,458,631 A | 10/1995 | Xavier |
| 5,523,092 A | 6/1996 | Hanson et al. |
| 5,533,986 A | 7/1996 | Mottola et al. |
| 5,545,151 A | 8/1996 | O'Connor |
| 5,549,603 A | 8/1996 | Feiring |
| 5,616,121 A | 4/1997 | McKay et al. |
| 5,647,859 A | 7/1997 | Lampropoulos et al. |
| 5,647,860 A | 7/1997 | Roth et al. |
| 5,665,076 A | 9/1997 | Roth et al. |
| 5,681,274 A | 10/1997 | Perkins et al. |
| 5,702,372 A | 12/1997 | Nelson |
| 5,785,678 A | 7/1998 | Griep et al. |
| 5,873,865 A | 2/1999 | Horzewski et al. |
| 6,017,323 A | 1/2000 | Chee |
| 6,117,125 A | 9/2000 | Rothbarth et al. |
| 6,179,816 B1 | 1/2001 | Mottola et al. |
| 6,193,704 B1 | 2/2001 | Winters |
| 6,235,009 B1 | 5/2001 | Skow |
| 6,235,788 B1 | 12/2001 | McKay |
| 6,350,253 B1 | 2/2002 | Deniega et al. |
| 6,514,517 B2 | 2/2003 | Jamiolkowski et al. |
| 6,524,300 B2 | 2/2003 | Meglin |
| 6,534,559 B1 | 3/2003 | Vanderlaan et al. |
| 6,558,686 B1 | 5/2003 | Darouiche |
| 6,569,839 B1 | 5/2003 | McKay |
| 6,626,885 B2 | 9/2003 | Massengale |
| 6,676,643 B2 | 1/2004 | Brushey |
| 6,689,110 B2 | 2/2004 | Brushey |
| 6,749,580 B2 | 6/2004 | Work et al. |
| D499,017 S | 11/2004 | Nestenborg |
| D499,643 S | 12/2004 | Nestenborg |
| 6,878,128 B2 | 4/2005 | MacMahon et al. |
| D505,067 S | 5/2005 | Nestenborg |
| 6,893,414 B2 | 5/2005 | Goble et al. |
| 6,921,541 B2 | 7/2005 | Chasin et al. |
| 7,001,371 B1 | 2/2006 | McLaughlin et al. |
| 7,004,923 B2 | 2/2006 | Deniega et al. |
| 7,100,771 B2 | 9/2006 | Massengale et al. |
| 7,119,062 B1 | 10/2006 | Alvis et al. |
| 7,186,247 B2 | 2/2007 | Ujhelyi et al. |
| 7,195,624 B2 | 3/2007 | Lockwood et al. |
| 7,201,745 B2 | 4/2007 | DiMatteo et al. |
| 7,232,425 B2 | 6/2007 | Sorenson et al. |
| 7,276,051 B1* | 10/2007 | Henley ............... A61M 1/0088 604/289 |
| 7,282,214 B2 | 10/2007 | Wilcox et al. |
| 7,326,196 B2 | 2/2008 | Olsen et al. |
| 7,438,711 B2 | 10/2008 | Deniega et al. |
| 7,452,353 B2 | 11/2008 | Dal Porto et al. |
| 7,462,165 B2 | 12/2008 | Ding et al. |
| 7,462,177 B2 | 12/2008 | Brushey et al. |
| 7,465,291 B2 | 12/2008 | Massengale |
| 7,510,077 B2 | 3/2009 | Massengale et al. |
| 7,510,550 B2 | 3/2009 | Deniega et al. |
| 7,527,609 B2 | 5/2009 | Deniega et al. |
| 7,534,224 B2 | 5/2009 | Triebes et al. |
| 7,547,302 B2 | 6/2009 | Porto et al. |
| 7,569,045 B2 | 8/2009 | Deniega et al. |
| 7,575,593 B2 | 8/2009 | Rea et al. |
| D605,757 S | 12/2009 | Sawyer |
| D605,758 S | 12/2009 | Schwartz et al. |
| 7,625,337 B2 | 12/2009 | Campbell et al. |
| 7,699,830 B2 | 4/2010 | Martin |
| 7,778,852 B2 | 8/2010 | Vasko et al. |
| 7,806,869 B2 | 10/2010 | Nilsson et al. |
| 7,815,604 B2 | 10/2010 | Massengale et al. |
| 7,780,638 B1 | 11/2010 | Deniega et al. |
| 7,828,790 B2 | 11/2010 | Griffin |
| 7,854,730 B2 | 12/2010 | Dal Porto et al. |
| 7,854,732 B2 | 12/2010 | Massengale et al. |
| 7,942,864 B2 | 5/2011 | Hynes |
| D640,787 S | 6/2011 | Chia et al. |
| 7,959,623 B2 | 6/2011 | Massengale |
| 8,157,759 B2 | 4/2012 | Castillejos |
| 8,216,176 B2 | 7/2012 | Randolph |
| 8,882,678 B2* | 11/2014 | Karwoski ............... A61B 5/08 600/541 |
| 2002/0007204 A1 | 1/2002 | Goode |
| 2002/0009095 A1 | 1/2002 | Van Doren et al. |
| 2002/0017296 A1 | 2/2002 | Hickle |
| 2002/0082547 A1 | 6/2002 | Deniega et al. |
| 2002/0177803 A1 | 11/2002 | Chappuis |
| 2003/0069541 A1 | 4/2003 | Gillis et al. |
| 2003/0069551 A1 | 4/2003 | Bradley, III et al. |
| 2003/0105511 A1 | 6/2003 | Welsh et al. |
| 2003/0181864 A1 | 9/2003 | Deniega et al. |
| 2004/0030281 A1 | 2/2004 | Goble et al. |
| 2004/0054338 A1 | 3/2004 | Byordi et al. |
| 2004/0073194 A1 | 4/2004 | Olsen et al. |
| 2004/0193262 A1 | 9/2004 | Shadduck |
| 2005/0085769 A1 | 4/2005 | MacMahon et al. |
| 2005/0177118 A1 | 8/2005 | Hoganson et al. |
| 2005/0192638 A1 | 9/2005 | Gelfand et al. |
| 2005/0272697 A1 | 12/2005 | Herzberg et al. |
| 2006/0015089 A1 | 1/2006 | Meglin et al. |
| 2006/0058731 A1 | 3/2006 | Burnett et al. |
| 2006/0184098 A1 | 8/2006 | Barnitz |
| 2006/0195059 A1 | 8/2006 | Freyman et al. |
| 2006/0229573 A1 | 10/2006 | Lamborne |
| 2006/0229586 A1 | 10/2006 | Farles |
| 2007/0005004 A1 | 1/2007 | Hynes |
| 2007/0010786 A1 | 3/2007 | Casey et al. |
| 2007/0049999 A1 | 3/2007 | Esch et al. |
| 2007/0106247 A1 | 5/2007 | Burnett et al. |
| 2007/0118096 A1 | 5/2007 | Smith et al. |
| 2007/0197959 A1 | 8/2007 | Panotopoulos |
| 2007/0219488 A1 | 9/2007 | Francescatti |
| 2008/0033324 A1 | 2/2008 | Cornet et al. |
| 2008/0045883 A1 | 2/2008 | Radojicic |
| 2008/0073239 A1 | 3/2008 | Duffield et al. |
| 2008/0119802 A1 | 5/2008 | Vetter et al. |
| 2009/0182304 A1 | 7/2009 | Deniega et al. |
| 2009/0184026 A1 | 7/2009 | Massengale et al. |
| 2010/0000666 A1 | 1/2010 | Deniega et al. |
| 2010/0222668 A1 | 9/2010 | Dalke et al. |
| 2011/0137267 A1 | 6/2011 | Phillips et al. |
| 2012/0330295 A1 | 12/2012 | Manwaring et al. |

FOREIGN PATENT DOCUMENTS

| | | |
|---|---|---|
| JP | 08-538960 A | 11/2008 |
| WO | 1980/001139 A1 | 6/1980 |
| WO | 1992/208514 A1 | 5/1992 |
| WO | 1995/017918 A1 | 7/1995 |
| WO | 1996/030064 A1 | 10/1996 |
| WO | 1996/040325 A1 | 12/1996 |
| WO | 1997/034655 A1 | 9/1997 |
| WO | 1998/018510 A1 | 5/1998 |
| WO | 2000/015277 A2 | 3/2000 |
| WO | 2001/005210 A2 | 1/2001 |
| WO | 2001/132068 A2 | 5/2001 |

(56) References Cited

FOREIGN PATENT DOCUMENTS

| WO | 2001/070322 A1 | 9/2001 |
|---|---|---|
| WO | 2004/101052 A2 | 11/2004 |
| WO | 2004/101052 A3 | 11/2004 |
| WO | 2005/110521 A1 | 11/2005 |
| WO | 2006/114637 A2 | 11/2006 |
| WO | 2006/114638 A2 | 11/2006 |
| WO | 2007/070096 A1 | 6/2007 |
| WO | 2007/142688 A1 | 12/2007 |
| WO | 2007/143179 A2 | 12/2007 |
| WO | 2009/009367 A2 | 1/2009 |
| WO | 2009/009367 A3 | 1/2009 |
| WO | 2012/040311 A2 | 3/2012 |

OTHER PUBLICATIONS

Innocoll, Inc., "Files US and Irish Patent Applications for its CollaRx® Bupivacaine Implant for the Management of Post-operative Pain," Mar. 29, 2007 10:49:32 AM, from http://www.innocollinc.com/.
Supplementary European Search Report for European patent application No. 08781266.5, dated Jun. 16, 2011, 9 pages.
International Preliminary Report on Patentability, for International application No. PCT/US2008/068998, dated Jan. 12, 2010, 1page.
International Search Report for International application No. PCT/US2008/068998, dated Feb. 25, 2009, 3 pages.
International Search Report for International application No. PCT/US2011/052524, dated Apr. 27, 2012, 6 pages.
English Abstract of JP 11-319103, dated Nov. 24, 1999, 1 pp.
English Abstract of JP 2008-538960, dated Nov. 13, 2008, 1 pp.

\* cited by examiner

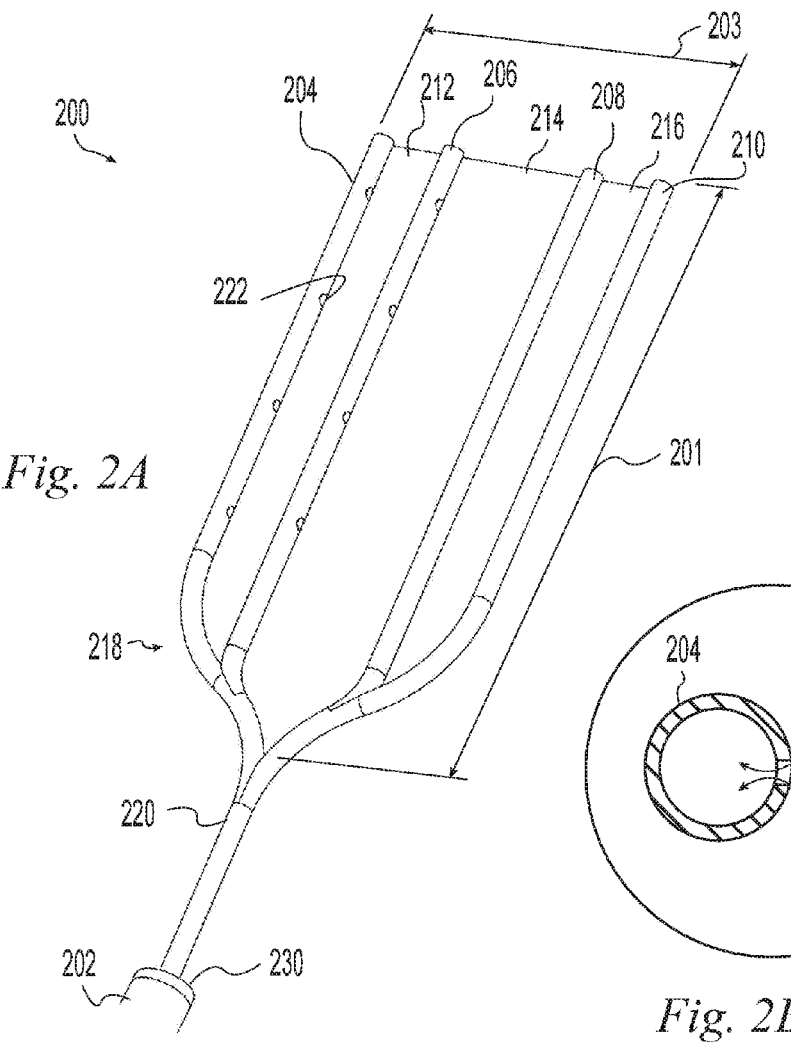
Fig. 2A
Fig. 2B
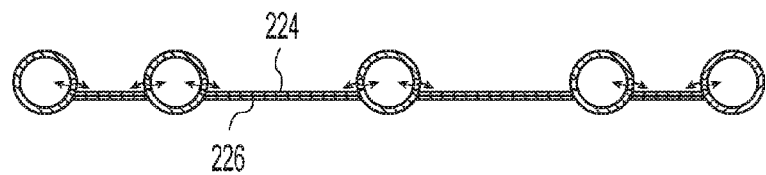
Fig. 2C

CATHETER ASSEMBLY

CROSS-REFERENCE TO RELATED APPLICATIONS

This application is a continuation of U.S. patent application Ser. No. 13/240,781 filed Sep. 22, 2011, which is a continuation-in-part of U.S. patent application Ser. No. 12/667,870, filed Jul. 2, 2008, each of which are herein incorporated by reference. U.S. patent application Ser. No. 13/240,781 claims the benefit of U.S. Provisional Application No. 61/385309, filed Sep. 22, 2010; U.S. Provisional Application No. 61/450,096, filed Mar. 7, 2011; and U.S. Provisional Application No. 61/494,822, filed Jun. 8, 2011, each of which is herein incorporated by reference.

FIELD OF THE INVENTION

The invention relates to devices and methods for transporting fluid to or from a treatment site of a patient's body.

BACKGROUND

Many medical procedures benefit from transporting fluid to or from a treatment site of a patient's body. Devices for transporting fluid in a medical procedure are generally referred to as catheters. They may be used to provide drainage or administer treatment fluids. For example, catheters may be used to drain fluids from organs or from areas of abnormal fluid collection such as in a surgical wound following a surgical procedure. Catheters may also be used to deliver fluid to a treatment site to provide a vast range of therapies from cancer treatment to nutritional supplementation. A few exemplary therapies include stimulating tissue growth, administering antibiotics, flushing away impurities, killing or halting the reproduction of cancer cells, and relieving pain.

Catheters may be used in gravity driven arrangements such as with a collection container located below the treatment site or a medication container located above the treatment site. Likewise, catheters may be used in pressurized arrangements. For example, suction may be applied to a drainage catheter to draw fluids away from the treatment site. Suction devices may include elastomeric bulbs, spring actuated bellows, electromechanical vacuum pumps, and other known medical suction devices. Pressurized fluid may also be delivered through a catheter to the treatment site. For example, fluid infusion devices may include manual syringes, elastomeric infusion devices, spring loaded infusion devices, electromechanical infusion devices, and other known infusion devices.

Typical prior catheters are linear devices having one or more openings formed along a portion of their length through which fluid passes. They often perform poorly due to an inability to drain fluids from or deliver fluids to a sufficiently large area to encompass the entire treatment site. In addition, tissue folds and tissue apposition further affect the movement and collection of fluid making it difficult for prior catheters to adequately address the treatment site.

For example, where a treatment site encompasses a two or three dimensional treatment area, prior drainage catheters are only able to drain fluid from a relatively small, linear portion of the treatment area often leaving behind pockets of fluid.

Similarly, prior infusion catheters only deliver treatment fluid to a relatively small, linear portion of the treatment site leaving much of the site untreated. Prior infusion catheters may also deliver too much treatment fluid to a relatively small area resulting in pooling of treatment fluid or contact with non-target tissues. For example, infusion catheters may be used to deliver pain relieving medication directly to a surgical site to provide, for example, post-operative relief of pain resulting from a surgical intervention. If, for example, the medication does not reach tissue disrupted during the surgical intervention, it may not relieve the pain. Alternatively, if the anesthetic is delivered indiscriminately, undesired interactions may occur with local structures such as, for example, spinal nerves or vital organs.

SUMMARY

Aspects of the invention provide devices and methods to conduct fluid away from or deliver fluid to an area of a treatment site of a patient's body. Fluid delivered to a treatment site will be referred to as treatment fluid and may be any material delivered to the treatment site to obtain a desired effect. For example treatment fluid may be water, saline, antibiotics, antiviral agents, hormones, growth factors, anti-inflammatories, analgesics, anesthetics, and/or any other material useful in treating a patient. For example, anesthetics may include marcaine, rupivicaine, bupivacaine, and/or any other anesthetic or combinations thereof The devices and methods of the illustrative examples maybe used in a variety of patient interventions. For example they may be used to deliver fluids to or remove fluids from a surgical site. For example they may be used to deliver medications to remove post-operative pain or drain fluids from a post-operative wound. Examples of such surgical procedures include surgery of the head, neck, chest, back, abdomen, and the extremities. Examples include general surgery, cosmetic surgery, joint surgery, and spine surgery. However, it will be apparent to one having skill in the art that the disclosed devices and methods may be used to treat a variety of other conditions by drainage of fluids from and delivery of fluids to a treatment site.

In one aspect of the invention, a catheter includes a first or connection end and an opposite, second or terminal end. A fluid conduit extends between the connection end and the terminal end for passing fluids. The terminal end includes a fluid exchange portion. The fluid exchange portion may include a hollow body having a wall defining the terminal end of the fluid conduit and one or more openings formed through the wall for passage of fluid between the fluid conduit and an exterior of the conduit. The catheter may include more than one fluid conduit. Multiple fluid conduits may provide the same or different functions. For example, the catheter may have one or more infusion conduits to conduct treatment fluid to a treatment site and one or more aspiration conduits to conduct fluids away from a treatment site. Infusion and aspiration conduits may be incorporated in the same catheter or they may be provided in separate catheters placed independently at a treatment site.

Conduits may be made of any suitable biocompatible material. For example, conduits may be made of a biocompatible polymer. For example, conduits may be made of a heat settable elastic polymer. For example, the conduit may be made of or contain a thermoplastic elastomer such as a styrenic block copolymer, polyolefin, thermoplastic polyurethane, thermoplastic copolyester, thermoplastic polyamide, and/or their various blends. For example, the conduit may contain or be made of a polyether block amide or PEBA. PEBA is available from Arkema under the tradename of PEBAX®.

The terminal end may include a diffuser having an outer surface. The diffuser may include a plurality of independent channels able to transport fluid between the conduit and discrete portions of the outer surface. The diffuser may include a network of interconnected pores able to distribute fluid throughout the diffuser and the outer surface. The diffuser may be permanently secured to the terminal end or removably secured to the terminal end. The diffuser may be placed separately at the treatment site independent of the terminal end. A separately placed diffuser may wick fluid to or from an area defined by an exterior surface of the diffuser. The diffuser may be resorbable or durable. The diffuser may be made of polymers, ceramics, metals, plant tissue, animal tissue, and/or other suitable materials. The diffuser may include fibers, fabric, sponge, textures and/or other suitable diffusing structures. For example, the diffuser may include a textured surface. The surface may be textured by stamping, knurling, roughening, and/or by other suitable means. The surface may also be textured by forming raised lines, bumps, ridges, and/or other suitable features. The texture may include fibers. The diffuser may include a network of fibers able to conduct fluid within, along, or between the fibers. The fibers may be adhered to a surface or free standing. For example, the network may be made by weaving, knitting, braiding, felting, bonding, and/or other suitable textile process. For example, the diffuser may include a fabric made of woven synthetic fibers in a generally planar arrangement and positionable between opposing tissues to transport fluid over an extended area by wicking fluid along and between the fibers via capillary action.

The terminal end may include a barrier to fluid flow to impede fluid flow in specific predetermined directions. The barrier may be connected to the one or more conduits to bias fluid flow in a preferential direction or to impede fluid flow in a non-preferential direction. The barrier may be permanently secured to the terminal end or removably secured to the terminal end. The barrier may be separate from the terminal end and placed relative to the terminal end to isolate selected portions of the patient's anatomy from the fluid flow. The barrier may, for example, impede fluid flow by juxtaposition of a fluid impervious structure and/or by absorption of fluid. The barrier may be made resorbable or durable. The barrier may be made of polymers, ceramics, metals, plant tissue, animal tissue, and/or other suitable materials. The barrier may be in the form of a block, sheet, film, layer, and/or other suitable form adapted or adaptable to the anatomic site where the barrier function is desired. The barrier may be provided pre-shaped and sized for a particular application and/or it may permit intraoperative shaping and sizing by the user. For example, the barrier may be made of a thin polymer film. In another example, the barrier may be made of collagen forming a relatively fluid impervious membrane. The barrier may be coupled to a diffuser to provide fluid flow through portions of the diffuser while blocking fluid flow through other portions of the diffuser.

The barrier and/or diffuser may separate tissue layers at the treatment site and maintain fluid communication between the tissue layers over a two-dimensional or three-dimensional treatment site to extend the effective treatment area. Furthermore, the barrier and/or diffuser may extend peripherally into the tissue folds and irregularities to separate tissue layers and enhance fluid transport between the layers and adjacent the barrier and/or diffuser. Enhancement of fluid transport reduces the number of catheters required to transport fluid to and/or away from the treatment site.

The one or more openings in the wall of the conduit may be positioned at any circumferential position around the wall. They may be placed parallel to the plane of the non-linear path of the terminal end so that they open within the space between tissue layers to avoid blocking of the openings by overlying tissue.

The barrier and/or diffuser may have a predetermined shaped that conforms to the margins of a particular surgical site. The shape may be polygonal, ovoid, spiral, or random shaped.

The terminal end of the catheter may have a first configuration and a second configuration into which it may be modified. For example, the terminal end may have a deployed configuration for fluid transport to or from a treatment site and a delivery or removal configuration. The delivery or removal configuration may be smaller than the deployed configuration to ease placement or removal of the terminal end at a desired location of a patient's anatomy. For example, the delivery or removal configuration may be folded, rolled, collapsed, stretched, compressed, twisted, deflated, straightened and/or otherwise manipulated relative to the deployed configuration.

The catheter may be placed at the treatment site in an inside-out placement method in which it is placed in an open wound and the connection end is passed out of the patient's body leaving the terminal end at the treatment site. Alternatively, the catheter may be placed at the treatment site in an outside-in placement method in which the terminal end is introduced from outside the patient's body to the treatment site. Where a surgical incision is present near the treatment site, the catheter may extend through the incision. Alternatively, the catheter may extend through another opening, such as a stab incision, formed for the purpose of passing a portion of the catheter.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2A is a perspective view of an embodiment of the invention;

FIG. 2B is a partial sectional view of the embodiment of FIG. 2A;

FIG. 2C is a cross-sectional view of a variation of the embodiment of FIG. 2A;

DESCRIPTION OF THE ILLUSTRATIVE EXAMPLES

Figure 1A:
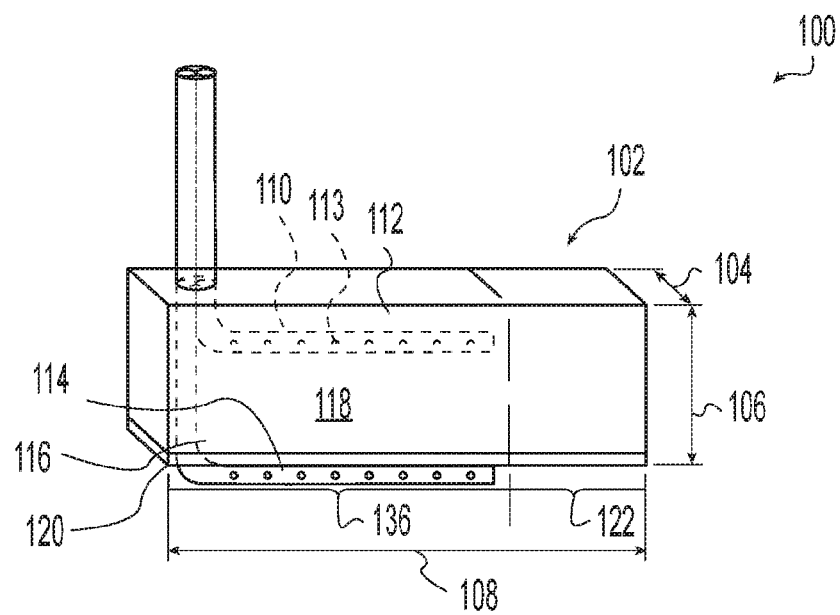
FIG. 1A is a perspective view of an embodiment of the invention.

FIG. 1 depicts an illustrative example of a fluid delivery device in the form of a terminal end 100 of a catheter for placement in a patient at a treatment site. The terminal end 100 includes a diffuser body 102 having a depth 104, width 106, and length 108. A first conduit 110 is positioned within the diffuser body 102 near a first portion 112 of the body 102. In use, fluid is transported between the first conduit 110 and the diffuser body 102. For example, wound fluid may be absorbed by the diffuser and transported to the first conduit 110 via small openings 113 through the conduit wall for removal from the treatment site. Alternatively, treatment fluid may be delivered by the first conduit 110 to the diffuser body 102 so that the fluid wicks through the diffuser body 102 to evenly wet a surface 118 of the diffuser body 102 and transfer to tissues adjacent to the surface 118 at the treatment site. Optionally, a second conduit 114 is positioned adjacent to the diffuser body 102 near a second portion 116 of the body 102. The conduits 110, 114 may be removably positioned allowing them to be withdrawn from the diffuser while leaving the diffuser in place after treatment has been concluded. In the illustrative example of FIG. 1A, the first conduit 110 is an infusion conduit and the second conduit is an aspiration conduit 114. The first, or infusion, conduit 110 delivers treatment fluid to the diffuser body. The aspiration conduit 114 collects and transports body fluid and excess treatment fluid away from the treatment site.

An optional fluid impermeable barrier 120 may be positioned on one or more surfaces of the diffuser body 102 to prevent fluid transport through the portion of the diffuser body 102 covered by the barrier. Selection of the diffuser shape, infusion conduit position and flow rate, aspiration conduit position and flow rate, and/or location of fluid barriers permits the treatment fluid delivery properties of the terminal end 100 to be tailored. In the illustrative example of FIG. 1, the infusion and aspiration conduits 110, 114 extend only partially along the length of the diffuser body 102 leaving a conduit-free, trimmable portion 122. The trimmable portion 122 is sized to be sufficiently short so that the fluid delivery to the trimmable portion 122 is not significantly less than the fluid delivery to the rest of the diffuser body 102. This trimmable portion 122 may be trimmed to fit the length of the terminal end 100 to the treatment site without cutting into a fluid conduit and without significantly changing the fluid delivery properties of the terminal end 100.

Figure 1B:
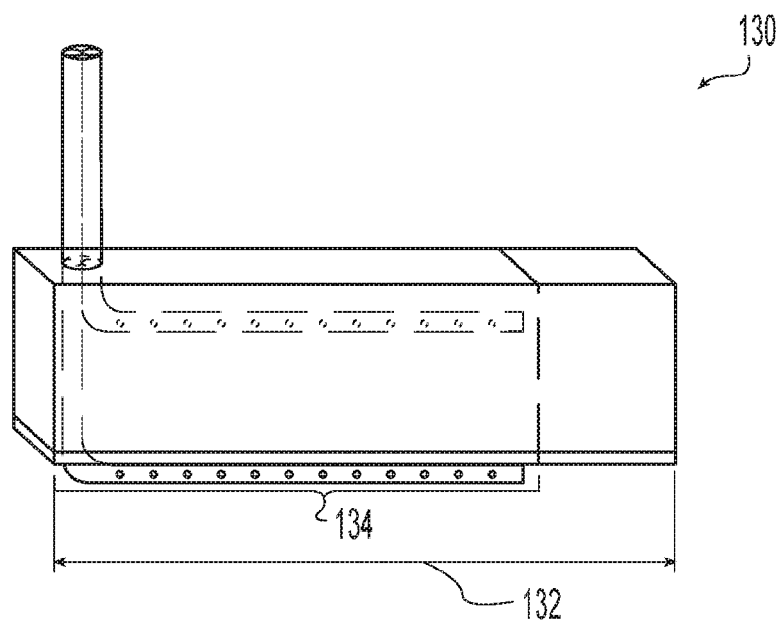
FIG. 1B is a perspective view of a size variation of the embodiment of FIG. 1A.

FIG. 1B illustrates how a second terminal end 130 may be provided having a different length 132 than the first terminal end 100 of FIG. 1A. The length 108 of the first terminal end 100 may be approximately equal to the fully trimmed length 134 of the second terminal end 130. By arranging the lengths in this way, it is possible to provide infinite adjustability of length within a range of possible lengths ranging from the fully trimmed length 136 of the first terminal end 100 to the length 132 of the second terminal end 130. Any number of terminal ends may be provided to cover a desired range of lengths. Likewise, trimmable portions may be provided to allow for adjustment of the depth and width of the diffuser body 102.

Figure 1C:
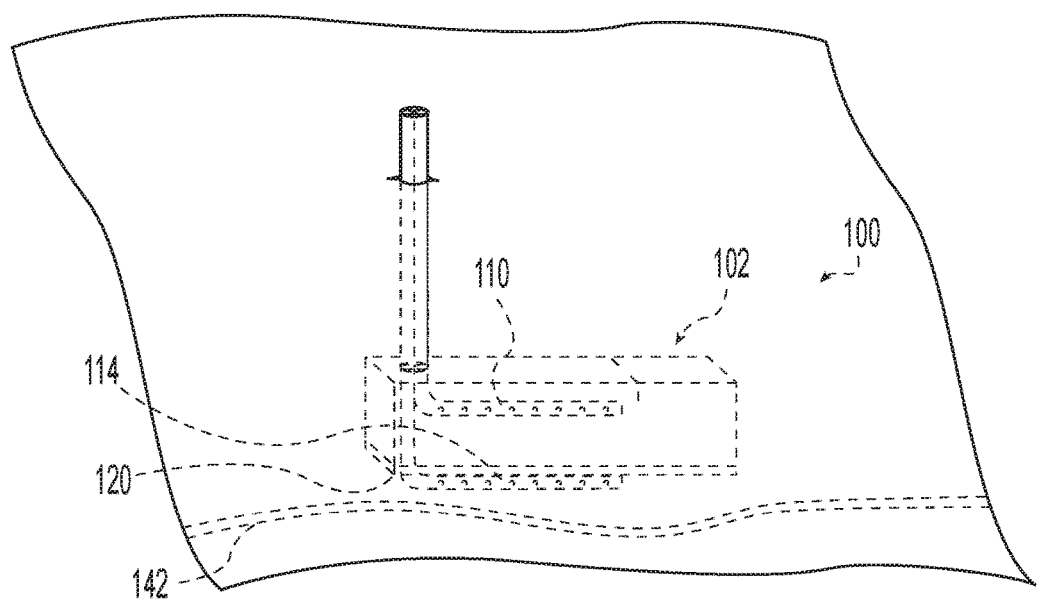
FIG. 1C is a perspective view of the embodiment of FIG. 1A shown in situ at a treatment site.

FIG. 1C depicts terminal end 100 placed in the depth of a surgical wound to deliver anesthetic to tissues disrupted during an operation on a patient's spine. The infusion conduit 110 and diffuser body 102 distribute the anesthetic over the surface of the diffuser body to treat adjacent tissues. The barrier 120 is positioned on a portion of the diffuser body 102 near a nerve root 142 to protect the nerve root 142 from anesthetic treatment fluid. The aspiration conduit 114 is positioned below the barrier 120 to aspirate body fluids and excess anesthetic.

FIG. 2 depicts a terminal end 200 of a catheter 202 having a length 201, a width 203, and a depth perpendicular to the length 201 and width 203. The end 200 may be formed integrally with the catheter 202 or the end 200 may be formed separately from the catheter 202 and joined to it, as shown. The end 200 includes a plurality of fluid conduits 204, 206, 208, 210. Adjacent conduits are connected by intermediate portions 212, 214, 216 that aid in spacing the conduits 204-210 in desired relative positions. The intermediate portion 212-216 may be in the form of a flexible sheet and the conduits 204-210 may be formed from shape memory tubing having a first, or rest, shape to which the tubing returns after being constrained to an alternate shape and then released. In the illustrative example of FIG. 2A, the conduits 204-210 are joined at a junction 218 to a common line 220. The conduits 204-210 are formed to spring away from one another as they extend away from the junction 218. Intermediate portions 212-216 constrain the conduits 204-210 to a generally parallel, palmate configuration. The conduits 204-210 include openings 222 formed through the conduit wall for passage of fluid between the interior and exterior of the conduits 204-210. In an infusion configuration, the intermediate portions 212-216 receive fluid exiting the openings 222 and distribute it over the surface of the terminal end 200. In an aspiration configuration, the intermediate portions 212-216 collect fluids from the treatment site for evacuation via the openings 222. The intermediate portions 212-216 and openings 222 may be positioned so that the openings 222 communicate with only one side of the intermediate portions 212-216 so that the terminal end 200 may be used to preferentially transport fluid to or from some portions of a treatment site. Alternatively, the intermediate portions 212-216 and openings 222 may be positioned so that some openings 222 communicate with one side of the intermediate members 212-216 and other openings 222 communicate with the other side of the intermediate members 212-216 to transport fluid to or from both sides of the terminal end 200. Alternatively, the openings 222 may be positioned so that an opening 222 communicates with both sides of the intermediate portions 212-216 simultaneously such as by positioning the opening 222 to communicate with both sides as shown in FIG. 2B. The intermediate portions 212-216 may have a fluid impervious surface that allows the fluid to flow across the surface to distribute it in a thin sheet-like fashion. The intermediate portions 212-216 may have porous surfaces so that they wick the fluid across an area. The intermediate portions 212-216 may be porous and permeable so that they wick the fluid through them between opposite sides of the intermediate portions 212-216. The intermediate portions 212-216 may include a laminate structure having an porous layer 224 on one side that wicks fluid and a fluid impervious layer 226 on an opposite side to impede fluid flow as shown in FIG. 2C.

While four fluid conduits 204-210 have been shown, it is to be understood that any number of conduits may be used. Furthermore, while tubular conduits have been depicted, conduits having any cross-sectional shape may be used including, for example, polygonal, curved, annular, and other cross-sectional shapes.

During delivery, the terminal end 200 can be folded and/or rolled into a small delivery configuration, not shown, and placed at the treatment site. The terminal end is then released whereupon the delivery conduits will tend to spring away from one another, as permitted by the surrounding tissue, into the configuration shown in FIG. 2A. In the illustrative example of FIG. 2, the common line 220 has an outside diameter less than that of the catheter 202 such that a step 230 is formed between them. This change in diameter facilitates removal of the terminal end 200 by withdrawal through an opening in the patient's body sized for the catheter 202. Pulling on the catheter 202 or common line 220 to extract the terminal end 200 from the treatment site tends to cause the conduits 204-210 to move toward one another due to pressure from surrounding patient tissues. The terminal end 200 collapses behind the step 221 to a constrained configuration approximately the same diameter as the catheter 202.

FIG. 3 depicts a terminal end 300 of a catheter 302 having a fluid infusion side 304 and a fluid aspiration side 306 and including a length 301, a width 303, and a depth 305. The terminal end 300 includes an elongated body 308 having a wall 310 (FIG. 3C) defining an outer surface 312 and one or more elongated aspiration lumens. In the illustrative example of FIG. 3, the wall 310 defines a single, centrally positioned aspiration lumen 314 in fluid communication with a corresponding aspiration conduit 316 (FIG. 3A) of the catheter 302. A plurality of aspiration openings 318 are spaced along the length of the elongated body 308 communicating from the aspiration lumen 314 to the outer surface 312 through the wall 310. The wall 310 further defines one or more elongated infusion lumens. In the illustrative example of FIG. 3, the wall defines two infusion lumens 320 extending parallel to the aspiration lumen 314 in fluid communication with corresponding infusion conduits 322 (one shown in FIG. 3A) of the catheter 302. A plurality of infusion openings 324 are spaced along the length of the elongated body 308 communicating from the infusion lumens 320 to the outer surface 312 through the wall 310. In the illustrative example of FIG. 3, the infusion openings 324 are oriented approximately 90 degrees relative to the aspiration openings 318.

A barrier 326 is attached to the outer surface 312 of the elongated body 308 adjacent the aspiration openings 318. In the illustrative example of FIG. 3, the elongated body 308 is "D"-shaped with a flat side. The barrier 326 is attached to the flat side along the length of the elongated body 308 and is configured to lie in a plane with the elongated body 308 projecting outwardly from it. The barrier 326 includes openings 328 aligned with and in fluid communication with the aspiration openings 318 to allow fluid flow from adjacent the barrier surface into the aspiration lumen. The barrier 326 is fluid resistant and separates the fluid aspiration side 306 from the fluid infusion side 304 of the terminal end 300. In the illustrative example of FIG. 3, the barrier is a fluid impermeable polyurethane membrane.

A diffuser 330 is attached to the outer surface 312 of the elongated body 308 opposite the barrier 326. In the illustrative example of FIG. 3, the diffuser 330 conforms to the curved surface of the elongated body 308 and is attached to the barrier 326. The infusion openings 324 communicate with the diffuser 330. In the illustrative example of FIG. 3, the diffuser is a woven polyester fabric that wicks treatment fluid throughout the diffuser via capillary action.

The infusion side 304 of the terminal end 300 infuses treatment fluid into a treatment site while the aspiration side 306 aspirates fluid away from a treatment site. The barrier 326 prevents fluid flow directly from the infusion openings 324 to the aspiration openings 318. The barrier 326 also isolates patient tissues on the aspiration side 306 from treatment fluid delivered by the infusion side 304.

In the illustrative example of FIG. 3, the catheter 302 has a larger diameter than the elongated body 308 and defines a step 334 between them. This change in diameter facilitates removal of the terminal end 300 by withdrawal through an opening in the patient's body sized for the catheter 302. Pulling on the catheter 302 to extract the terminal end 300 from the treatment site tends to cause the terminal end 300 to collapse behind the step 334 for easier passage through the tissue opening.

Figure 3A:
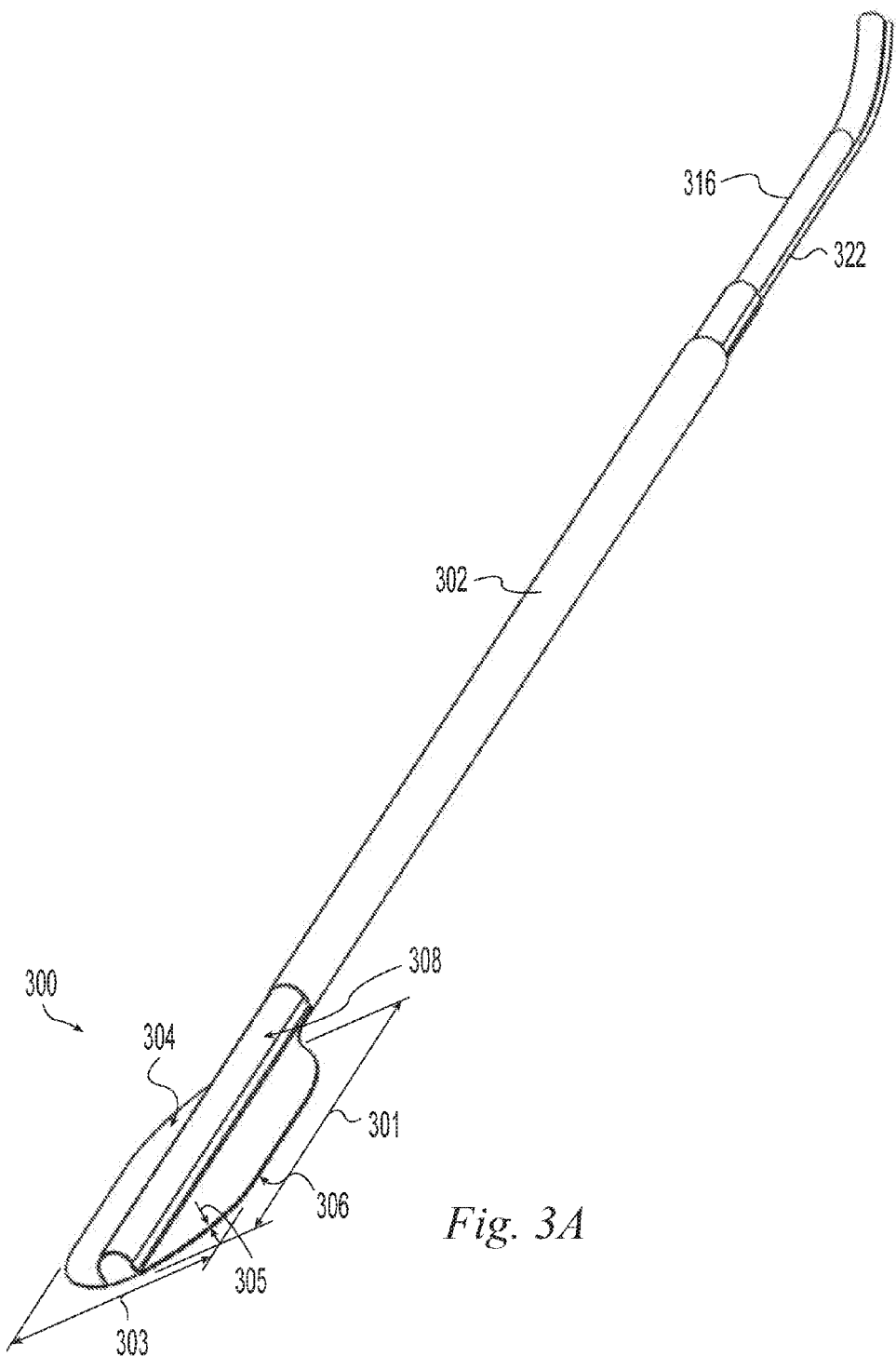
FIG. 3A is a bottom perspective view of an embodiment of the invention.
Figure 3B:
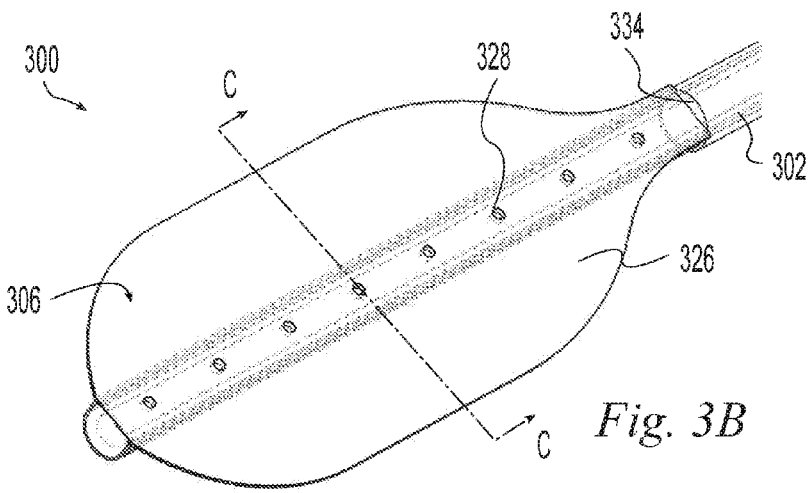
FIG. 3B is a top perspective view of the embodiment of FIG. 3A.
Figure 3C:
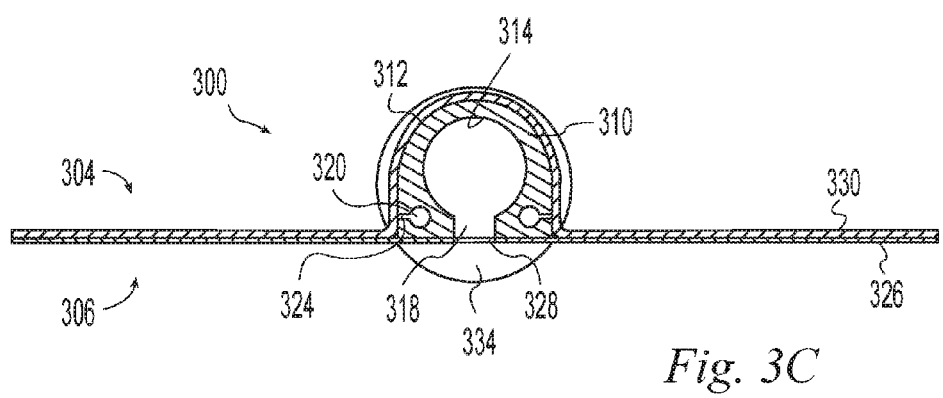
FIG. 3C is a cross-sectional view taken along line C-C of FIG. 3B.
Figure 3D:
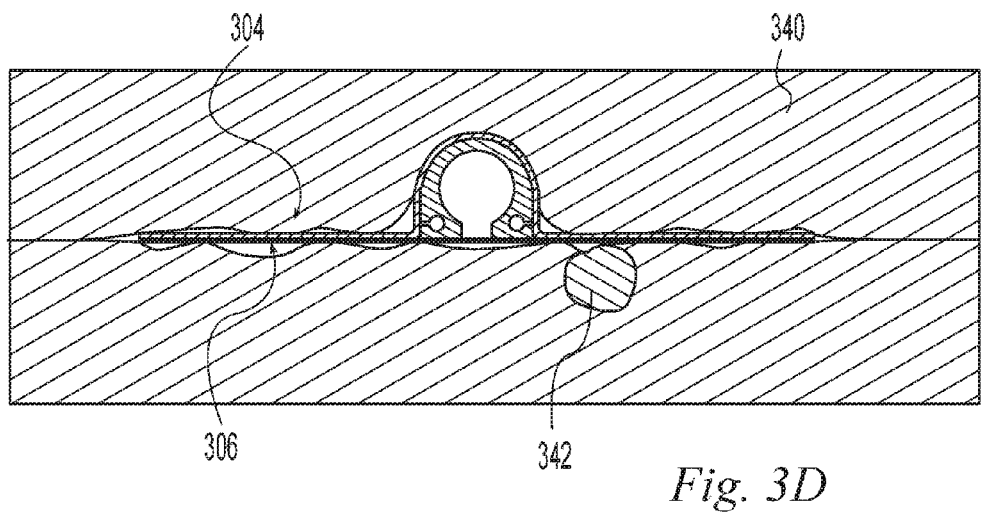
FIG. 3D is a cross-sectional view of the embodiment of FIG. 3A shown in situ at a treatment site.

FIG. 3D illustrates the terminal end 300 placed in tissue 340 that has been disrupted during a surgical procedure. The infusion side 304 is oriented toward tissues to be treated with treatment fluid and the aspiration side 306 is oriented toward an area to be drained and/or isolated from treatment fluid such as a nerve root 342. In use, for example, the infusion conduits 322 of the catheter are attached to a source of treatment fluid and the aspiration conduit 316 is attached to a vacuum source. Treatment fluid flows along the infusion lumens 320 and out through the infusion openings 324 where it enters the diffuser and is wicked throughout the diffuser and into contact with tissues adjacent to the infusion side 304 of the terminal end of the catheter. Body fluids and excess treatment fluid flow through the aspiration openings 318, into the aspiration lumen 314, and out through the aspiration conduit 316. The tissue 340 is treated while the nerve 342 is protected from the treatment fluid and the surgical wound is drained.

Figure 4A:
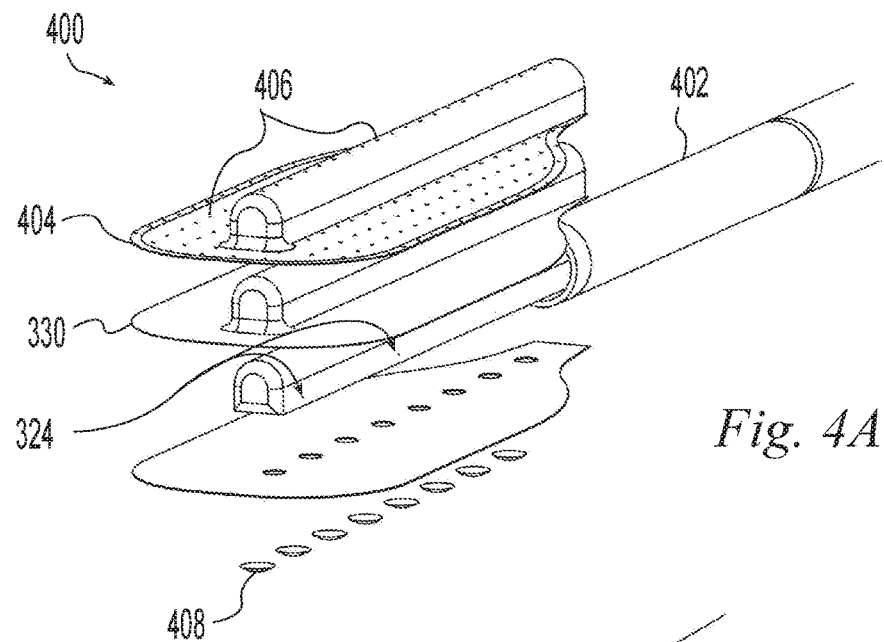
FIG. 4A is an exploded perspective view of an embodiment of the invention.
Figure 4B:
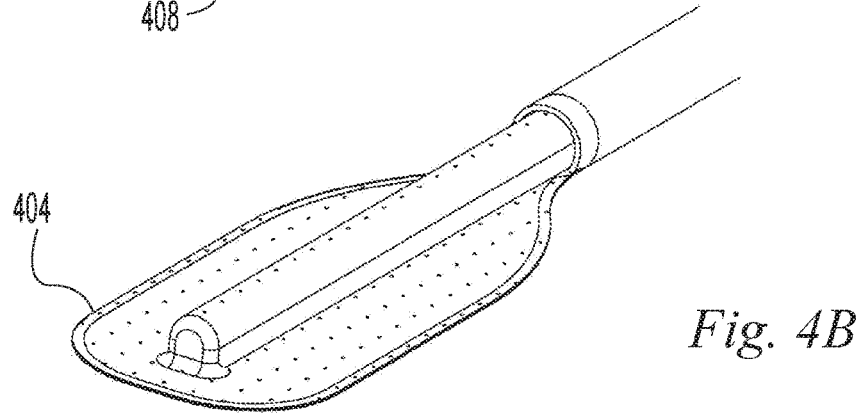
FIG. 4B is a top perspective view of the embodiment of FIG. 4A.
Figure 4C:
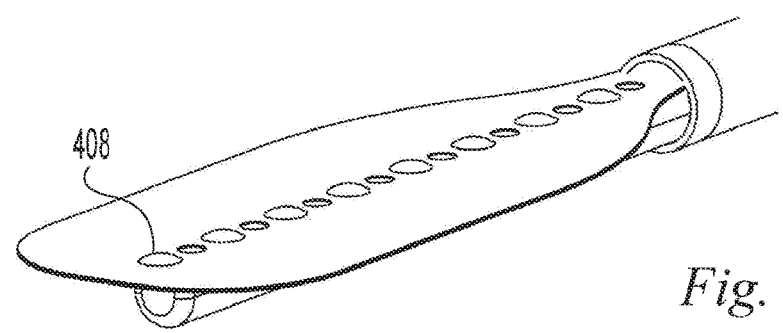
FIG. 4C is a bottom perspective view of the embodiment of FIG. 4A.

FIGS. 4A-C depict a terminal end 400 of a catheter 402 similar to that of FIG. 3 but having an additional member 404 covering the diffuser 330. In the illustrative embodiment of FIGS. 4A-C, the member 404 conforms closely to the diffuser 330 to separate the diffuser from surrounding tissue to prevent tissue from adhering to the diffuser. The member 404 may be in the form of a tissue growth inhibiting membrane. For example, the member 404 may be a fluid impermeable polyurethane membrane. The member 404 is perforated with a plurality of holes 406 to permit fluid dispersed through the diffuser to exit the terminal end 400.

The embodiment of FIGS. 4A-C further includes projections 408 creating a textured surface to improve fluid flow through adjacent openings. The projections prevent adjacent tissue from pressing against, or being drawn into, and sealing the openings. In the illustrative example, the projections are a plurality of bumps alternating with openings 328 to improve drainage from the surgical site. However, the projections 408 may be distributed across the surface in a two-dimensional pattern or elsewhere on the terminal end 400 to improve fluid flow. The projections may be molded integrally with the surface, adhered to the surface, formed by deforming the surface, deposited, cast, and/or otherwise formed. For example, the projections 408 may be formed by depositing a liquid compound and causing it to cure into a solid polymer such as a UV curable adhesive.

Figure 5A:
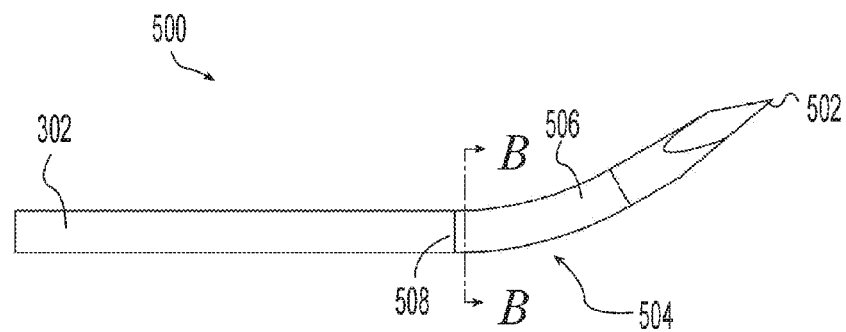
FIGS. 5A and 5B are perspective views of an embodiment of the invention.
Figure 5B:
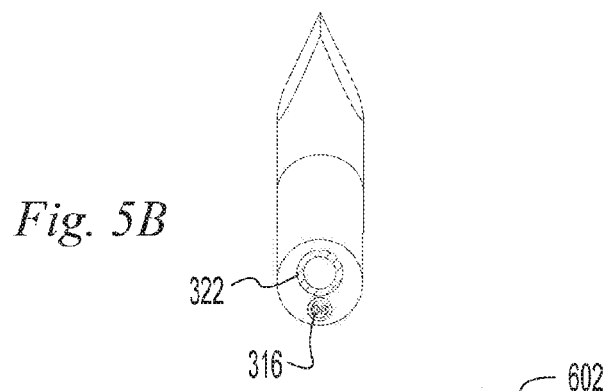

FIG. 5 illustrates an example of how the infusion and aspiration conduits 322, 316 may be configured for insertion through tissues adjacent a treatment site in an inside-out placement method. A trocar 500 includes a leading end with a sharpened tip 502 for penetrating tissue and a hollow trailing end 504 for receiving the catheter 302. The trailing end 504 includes a tubular outer wall 506 defining an opening 508 at an end opposite the tip 502. The aspiration and infusion conduits 322, 316 are received through the opening 506 into the trailing end. The trocar 500 and catheter 302 remain joined by friction until a sufficiently large force is applied to overcome friction or the end of the catheter 302 is cut.

Figure 6:
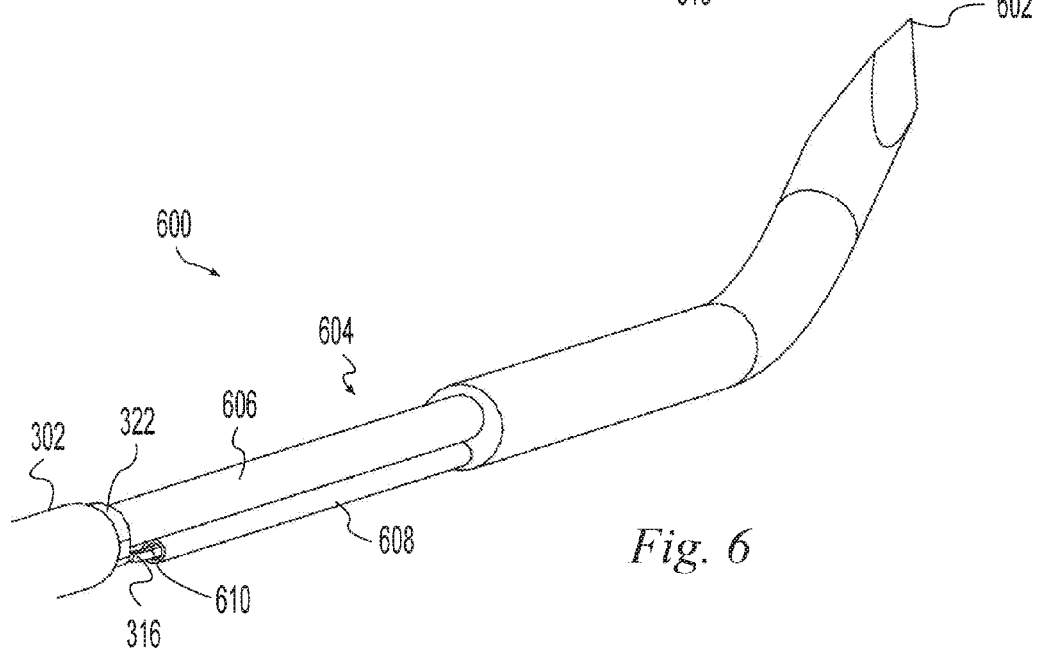
FIG. 6 is a perspective view of an embodiment of the invention.

FIG. 6 illustrates an alternate configuration for passing the catheter 302. A trocar 600 includes a leading end with a sharpened tip 602 for penetrating tissue and a trailing end 604 including first and second barbs 606, 608. The first barb 606 is sized for insertion into the aspiration conduit 322 in tight friction fitting relationship. The second barb 608 is hollow with an interior bore 610 sized to receive the infusion conduits 316.

Figure 7:
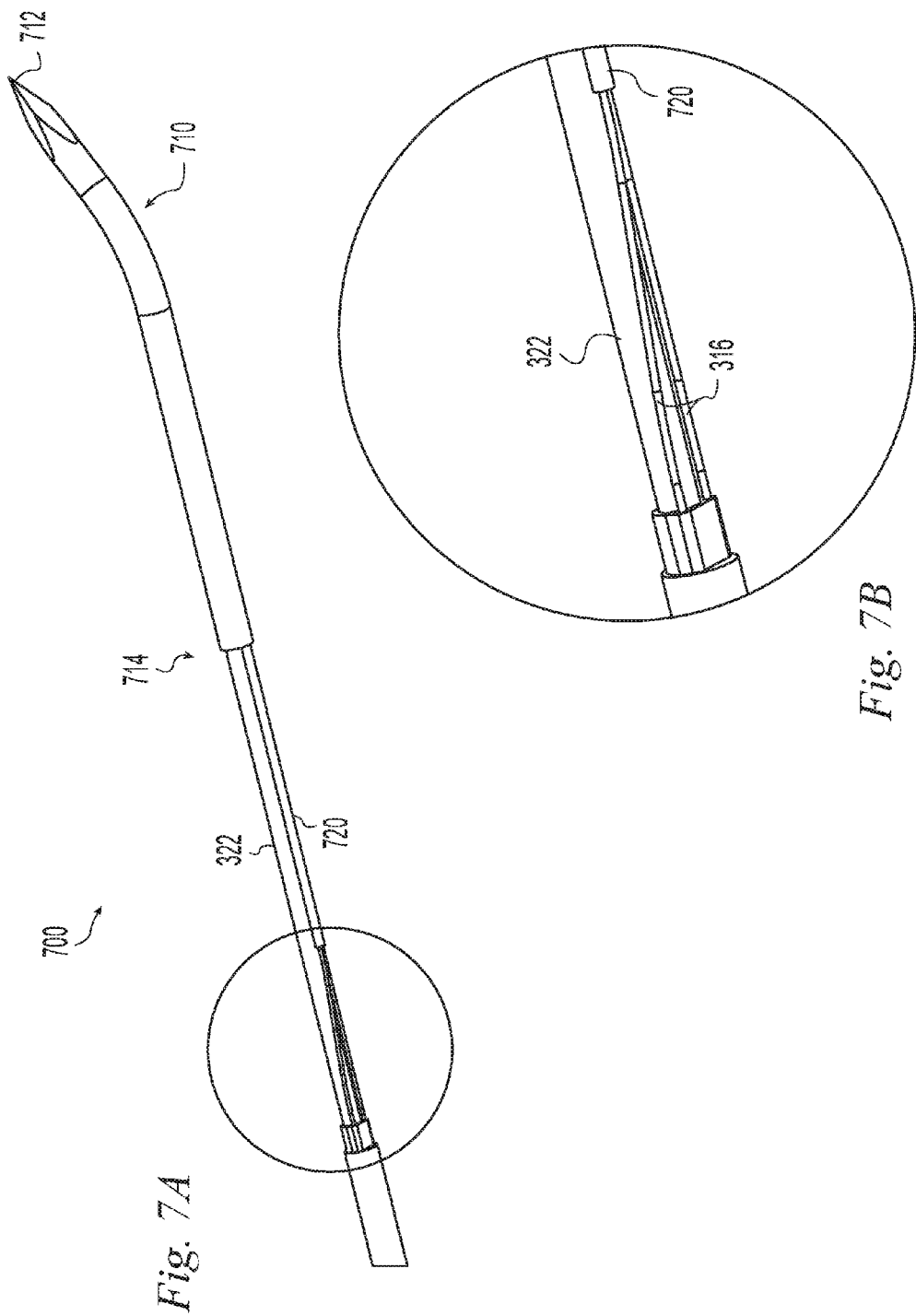
FIG. 7A is a perspective view of an embodiment of the invention.
FIG. 7B is a detail view of a portion of the embodiment of FIG. 8A.

FIG. 7 illustrates a catheter 302 and a passing configuration similar to the prior examples. However, in the example of FIG. 7 the infusion conduits 316 are inserted into an infusion common line 720 in fluid communicating relationship and sealed to the common line 720 such as with, for example, a UV curable potting adhesive as is commonly used with medical fluid tubing. This arrangement reduces the number of infusion conduits 316 that must be connected to an infusion apparatus and eliminates the need for a separate "Y"-connector by providing a single, common line 720 that can be connected. The trocar 710 includes a leading end with a sharpened tip 712 for penetrating tissue and a hollow trailing end 714 for receiving the aspiration conduit 322 and common line 720.

Figure 8:
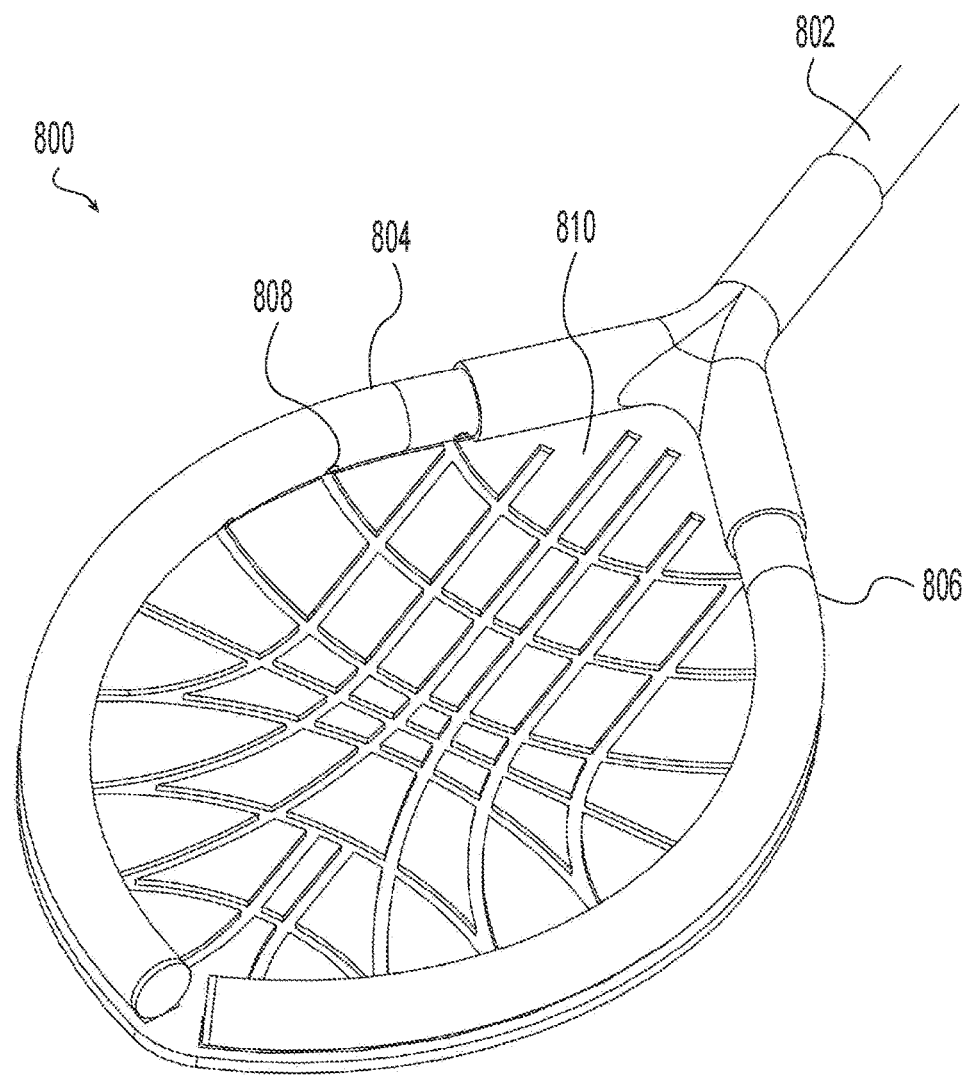
FIG. 8 is a perspective view of an embodiment of the invention.

FIG. 8 depicts a terminal end 800 of a catheter 802. The terminal end 800 includes fluid conduits 804, 806 that curve in an elliptical path and transport fluid to or from openings 808 on the interior of the elliptical path. A barrier 810 receives the fluid and distributes it along a textured surface. In the illustrative example of FIG. 8, the texture is provided by grooves 812 formed into the barrier 810. The grooves 812 aid in fluid flow by wicking fluid across the fluid impervious barrier 810 surface. The fluid might otherwise be blocked by abutment of patient tissues. The barrier 810 surface may be textured by stamping, knurling, roughening, and/or by other suitable means. The barrier surface may also be textured by forming raised lines, bumps, ridges, and/or other suitable features. The barrier surface may be textured by adhering a textile to the surface. For example a network of fibers may be adhered to the surface so that fluids may wick across the surface. Each of the various examples of terminal ends described herein have a length, a width, and a depth. The length of the terminal end may vary over a broad range to suit a variety of treatment sites. For example, the length may range from a few millimeters to tens of centimeters. In particular, the length may range from 1 to 30 centimeters. More particularly the length may range from 5 to 20 centimeters. The width of the terminal end may vary over a broad range to suit a variety of treatment sites. For example, the width may range from a few millimeters to tens of centimeters. In particular, the width may range from 0.5 to 30 centimeters. More particularly the width may range from 1 to 15 centimeters. The depth of the terminal end may vary over a broad range to suit a variety of treatment sites. For example, the depth may range from a fractions of a millimeter to tens of millimeters. In particular, the depth may range from 0.5 to 20 millimeters. More particularly the depth may range from 0.5 to 10 millimeters.

A treatment kit may be provided including one or more catheters according to various aspects of the invention. Optionally, the kit may include a diffuser. Optionally, the kit may include a protective barrier that may be placed separately from the catheter to shield specific tissues. Optionally, the kit may include an infusion pump.

In describing aspects of the invention, various examples have been described. It is to be understood that the features from one example may be incorporated into other examples.

What is claimed is:

1. A catheter comprising:
a terminal end having a first end and a second end;
an infusion conduit configured to provide a fluid pathway in the terminal end;
an aspiration conduit configured to provide a fluid pathway in the terminal end;
an elongated body extending between the first end and the second end, the elongated body having a longitudinal axis and defining an outer periphery, the elongated body being in fluid communication with the infusion conduit and the aspiration conduit;
a sheet-like member joined to the elongated body, the sheet-like member having an aspiration side and an infusion side, the aspiration and infusion sides in opposition to one another and not in fluid communication with one another through the sheet-like member, the sheet-like member defining a width extending transversely to the longitudinal axis beyond the periphery of the elongated body, the sheet-like member having a thickness less than the width, the infusion side of the sheet-like member defining a plurality of infusion openings, the infusion openings of the infusion side in fluid communication with the infusion conduit and not in fluid communication with the aspiration conduit, the aspiration side of the sheet-like member defining a plurality of openings, the openings of the aspiration side in fluid communication with the aspiration conduit and not in fluid communication with the infusion conduit.

2. The catheter of claim 1, wherein the infusion conduit includes a pair of fluid pathways between the first end and the second end.

3. The catheter of claim 1, wherein the sheet-like member comprises a diffuser on the infusion side.

4. The catheter of claim 3, wherein the sheet-like member further comprises a perforated member configured to cover the diffuser, the perforated member defining the plurality of infusion openings, the infusion openings being in fluid communication with the diffuser, the perforated member having an outer surface disposed away from the diffuser.

5. The catheter of claim 4, wherein the perforated member includes an anti-adhesion material effective to discourage tissue adhesion to the outer surface.

6. The catheter of claim 3, wherein the diffuser includes a fabric.

7. The catheter of claim 3, wherein the diffuser includes a woven fabric.

8. The catheter of claim 3, wherein the diffuser includes a woven polyester fabric configured to wick treatment fluid via capillary action.

9. The catheter of claim 3, wherein the diffuser includes a textured surface defining channels.

10. The catheter of claim 3, wherein the sheet-like member comprises a fluid impervious barrier opposite the diffuser.

11. The catheter of claim 10, wherein the barrier includes a polymer film.

12. The catheter of claim 1, further comprising a series of projections disposed on the fluid aspiration side of the sheet-like member.

13. The catheter of claim 12, wherein the series of projections alternate with the openings on the fluid aspiration side.

14. The catheter of claim 12, wherein the series of projections are configured to extend in a direction perpendicular to the longitudinal axis and perpendicular to the transversely extending sheet-like member.

15. The catheter of claim 1, wherein the sheet-like member has a generally rectangular shape.

16. The catheter of claim 1, further comprising a step formed at the second end and facing the first end and wherein the sheet-like member is configured to collapse behind the step so as to facilitate passage of the sheet-like member through patient tissues when the sheet-like member is withdrawn in a direction toward the second end.

17. The catheter of claim 16, wherein the sheet-like member includes a leading edge disposed toward the second end, and the leading edge is configured to transition the sheet-like member from a deployed configuration with the sheet-like member extending beyond the periphery to a collapsed configuration with the sheet-like member collapsed behind the step when the sheet-like member is withdrawn in a direction toward the second end.

18. The catheter of claim 1 wherein the elongated body comprises an elongated member extending between the first and second end and containing the infusion conduit and the aspiration conduit.

19. The catheter of claim 18 wherein the infusion conduit has a cross sectional area and the aspiration conduit has a cross sectional area, the aspiration conduit cross sectional area being greater than the infusion conduit cross sectional area.

20. The catheter of claim 19 wherein the elongated body includes openings along opposite sides thereof, the elongated body openings being in fluid communication with the infusion conduit and the infusion side of the sheet-like member.

* * * * *